United States Patent [19]
Evans

[11] Patent Number: 5,586,972
[45] Date of Patent: Dec. 24, 1996

[54] CREPE EFFECT BANDAGE

[75] Inventor: John C. Evans, Newhey, United Kingdom

[73] Assignee: Smith & Nephew plc, London, United Kingdom

[21] Appl. No.: 331,631

[22] PCT Filed: May 10, 1993

[86] PCT No.: PCT/GB93/00958

§ 371 Date: Nov. 7, 1994

§ 102(e) Date: Nov. 7, 1994

[87] PCT Pub. No.: WO93/22994

PCT Pub. Date: Nov. 25, 1993

[30] Foreign Application Priority Data

May 9, 1992 [GB] United Kingdom ............... 9210036

[51] Int. Cl.$^6$ ............................................. A61L 15/00
[52] U.S. Cl. .......................... 602/76; 602/41; 602/75; 66/195; 428/225
[58] Field of Search ................. 602/6, 8, 17, 18, 602/19, 20, 23, 5, 41, 44, 60, 75, 76, 900; 428/224, 225; 66/170, 195, 196

[56] References Cited

U.S. PATENT DOCUMENTS

| | | | |
|---|---|---|---|
| 4,236,550 | 12/1980 | Braun et al. | 602/76 |
| 4,424,808 | 1/1984 | Schafer et al. | 602/76 |
| 4,572,171 | 2/1986 | Wegner et al. | 602/8 |
| 4,761,321 | 8/1988 | McCall et al. | 428/176 |
| 4,940,047 | 7/1992 | Richter et al. | 128/90 |
| 5,256,134 | 10/1993 | Ingham | 602/8 |

*Primary Examiner*—Corrine M. McDermott
*Attorney, Agent, or Firm*—Larson and Taylor

[57] ABSTRACT

There is described a woven bandage which exhibits a crepe effect and which contains composite warp yarns (1) and weft filaments (7) wherein the composite warp yarns (1) are formed by twisting a staple fiber yarn (2) and a textured filament yarn (3) together. The staple fiber yarn (2) forms loops (4) which gives the bandage a crepe effect. There is also described a process for the manufacture of such woven bandages and an article of manufacture which includes the composite warp yarns used in the woven bandage.

21 Claims, 2 Drawing Sheets

CREPE EFFECT BANDAGE

The present invention relates to bandages which exhibit a crepe effect and to processes for the manufacture thereof.

Crepe bandages are normally used to provide light support and low compression for example in the treatment of sprains and strains and varicose veins. These bandages have sufficient elasticity to enable them to conform to the bandaged area and when secured, to allow limited movement and swelling to take place so that the circulation is not adversely affected. Crepe bandages normally comprise a woven fabric strip or tape containing high twist cotton warp yarns which are usually present in pairs with opposite twist in approximately equal numbers. These high twist warp yarns shrink when the woven fabric is treated for example by boiling in a vat to provide the bandage with elastic stretch and properties and a crepe appearance. However, high twist cotton yarns provide the bandage with a relatively harsh "feel" which can irritate sensitive skin areas. Furthermore, high twist cotton yarns used in conventional crepe bandages usually comprise in excess of 2000 turns per meter of yarn and are thus relatively expensive to manufacture.

U.S. Pat. No. 4,236,550, describes a bandage which comprises elastic and non-elastic threads. However, the bandages described therein possess relatively high elasticity and are therefore not suitable for use as support dressings in the same manner as a crepe bandage. Indeed U.S. No. 550 describes the disclosed dressings as being Useful as "a fixing band".

We have now found a woven bandage which avoids the use of high twist cotton yarns and thereby any problems associated with the use of these yarns and exhibits a crepe effect.

According to the present invention we provide a woven bandage which exhibits a crepe effect and which contains composite warp yarns comprising a staple fibre yarn and a textured filament yarn twisted together.

The bandage according to the invention may comprise warp yarns which are only made of the aforementioned composite. However, in addition, cheaper and more lightweight bandages may be prepared by utilising alternate composite yarns and textured filament yarns.

According to the invention we provide a woven bandage which exhibits a crepe effect and which contains textured filament yarns and composite yarns as hereinbefore described. Such a bandage may have 1–3 textured filament yarns for every composite yarn although we prefer such a bandage to comprise one textured filament-yarn for every composite yarn.

Preferably the textured filament yarns and composite yarns alternate but when the ratio of textured filament to composite yarns is greater than 1:1 the textured filament yarns are preferably in repeating patterns, e.g.

```
| | | | | | | | |
C T T C T T C T C
| | | | | | | | |
``` where C=a composite filament in the warp direction

T=a textured filament in the warp direction.

By the term crepe effect we mean that known in the art, that is, e.g. having a crinkled or puckered surface.

Composite warp yarns used in the woven bandage of the invention are formed of loosely twisted staple fibre and textured filament yarns. Bandages of the invention therefore do not contain any of the high twist yarns used in conventional crepe bandages.

The twist level for the composite yarn can suitably be from 60 to 200 turns/meter, preferably less than 140 turns/meter and preferably less than 130 turns/meter. Similarly the twist level for the composite yarn can be suitably at least 80 turns/meter and preferably at least 100 turns/meter. Apt twist levels for the composite yarn are 120–130 turns/meter for example 125 turns/meter.

The composite warp yarns used in the bandage of the invention are novel per se.

Thus according to the invention we also provide a composite yarn comprising a staple fibre yarn and a textured filament yarn twisted together and comprising from 60 to 200 turns.

The staple fibre yarns used in the invention are usually characterised by having only limited or no elasticity and good moisture absorption properties.

Suitable staple fibre yarns for use in composite warp yarns of bandages of the invention include staple cellulosic fibre yarns such as cotton fibre or staple viscose rayon fibre yarns. Such fibre yarns are hydrophilic in nature and therefore can advantageously provide the bandage with absorbent properties.

Preferred staple fibre yarns for use in the invention are cotton fibre yarns. Apt yarns of this type are known as 19.68 Tex and 36.9 Tex (cotton count) cotton yarns.

Composite yarns comprising a cotton yarn and a textured polyamide yarn are novel per se. Thus according to the invention we also provide a composite yarn comprising a cotton yarn and a textured yarn twisted together.

By the term textured yarn we mean a continuous filament yarn that has been processed to introduce durable crimps, coils, loops or other fine distortions along the lengths of the filaments.

The main texturing procedures which are usually applied are conventional procedures known per se, and include;

(a) the yarn is highly twisted, heat-set and untwisted either as a process of three separate stages or as a continuous process (false-twist texturing). In an infrequently used alternative method, two yarns are continuously folded together, heat-set then separated by unfolding;

(b) the yarn is injected into a heated stuffer box either by feed rollers or through a plasticizing jet of hot fluid (invariably air or steam). The jet process is sometimes known as jet texturing, hot-air jet texturing, or steam-jet texturing;

(c) the yarn is plasticized by passage through a jet of hot fluid and is impacted on to a cooling surface (impact texturing);

(d) the heated yarn is passed over a knife-edge (edge crimping);

(e) the heated yarn is passed between a pair of gear wheels or through some similar device (gear crimping);

(f) the yarn is knitted into a fabric that is heat-set and then unravelled (knit-deknit texturing);

(g) the yarn is over-fed through a turbulent air stream (air-texturing, air-jet texturing), so that entangled loops are formed in the filaments;

(h) the yarn is composed of bicomponent fibres and is subjected to a hot and/or wet process whereby differential shrinkage occurs.

Suitable textured filament yarns for use in composite warp yarns or as textured filament yarns alone in bandages of the invention include textured filament yarns of synthetic fibre polymers such as polyamide or polyester. Preferred textured filament yarns for use in the invention are textured polyamide filament yarns, e.g. nylon such as nylon 6,6. Apt yarns of this type are known as 2/78 D Tex nylon.

Preferred textured filament warp yarns for use as untwisted yarns are textured polyamide filament yarns such as 2/78 D Tex nylon filament yarns.

The textured filament warp yarns used in the invention will normally be in a tensioned state during weaving.

Textured filament yarns used in the invention suitably have a crimp rigidity of from 20–50%, at least 30% favourably at least 35% and preferably have a crimp rigidity of at least 40% for example 45%. The crimp rigidity of the textured yarns used in the invention can be determined according to the method given in British Standards Specification No. 6663.

Bandages according to the invention may contain conventional weft yarns. Suitable weft yarns for use in the bandage according to the invention include any of the staple fibre yarns hereinbefore mentioned in relation to the composite warp yarns, e.g. cellulosic fibre yarns such as cotton fibre or staple viscose rayon fibre yarns.

Preferred weft yarns are cotton yarns such as 19.68 Tex and 36.9 Tex cotton yarns.

Woven bandages of the invention can conveniently be light-weight or heavy-weight bandages. The bandages according to the invention suitably have a weight per unit area of 40 to 120 g/m$^2$.

Light-weight bandages according to the invention have a weight per unit area of 40–60 g/m$^2$ preferably 50–60 g/m$^2$. Heavy-weight bandages according to the invention have a weight of 60–120 g/m$^2$, preferably to 90 g/m$^2$.

One favoured embodiment of the invention is a bandage which comprises 19.68 Tex cotton/2/78 D Tex polyamide composite warp yarns which alternate with 2/78 D Tex polyamide warp yarns and 19.68 Tex cotton weft yarns, e.g. a light-weight bandage.

A second favoured embodiment of the invention is a bandage which comprises 19.68 Tex cotton/2/78 D Tex polyamide composite warp yarns only and 36.9 Tex cotton weft yarns, e.g. a heavy-Weight bandage.

Bandages of the invention can conveniently be woven on a fabric loom e.g. a narrow fabric loom in widths of 2.5 to 25 cm, preferably 5 to 20 cm for example in widths of 5, 7.5, 10 or 15 cm. The woven bandage can suitably contain 80 to 300 ends per 10 cm, e.g. 100 to 200 ends per 10 cm, preferably 130 to 170 ends per 10 cm and more preferably contain 140 to 160 ends per 10 cm. Similarly the woven bandage can suitably contain 50 to 110 picks/10 cm and preferably contain 60 to 80 picks/10 cm.

Bandages of the invention stretch in the warp direction to render the bandage conformable to a body portion to which it is to be applied.

A bandage of the invention can stretch in the warp direction. The extent to which a bandage may stretch depends, inter alia, on the number of twists of staple fibre yarn around the textured filament yarn. Suitably a bandage of the invention can stretch by at least 50% and preferably by at least 60% of its original length. Apt bandages of the invention have a stretch in the warp direction of 50 to 100% for example 70–80% of its original length.

The stretch is measured by subjecting the bandage to a load of 1 Kg/cm, according to British Pharmacopoeia Methods of Test for Surgical Dressings—Appendix XXF—Elasticity.

According to the invention we also provide an article comprising the bandage material according to the invention. Such articles may include, inter alia, a tubular bandage or an article of clothing.

According to a further feature of the invention we provide a method of treatment of one or more of the following disorders; namely, varicous veins, lymphodoeama, muscle strain or muscle sprain, which comprises applying a bandage or article according to the invention to the affected site on a patient.

We further provide the use of a bandage or article according to the invention in the treatment or alleviation of varicous veins, lymphodoema, muscle strain or muscle sprain.

Bandages of the invention exhibit a crepe effect. Such an effect is produced by shrinking the woven bandage fabric.

Composite yarns according to the invention are manufactured using am uptwister, preferably an enamel uptwister, using conventional methods known per se.

Therefore in another aspect the present invention provides a process for making a bandage of the invention which comprises treating a woven bandage fabric containing composite warp yarns comprising a staple fibre yarn and a textured filament yarn to shrink the fabric in the warp direction.

During the process the bandage is woven in a tensioned state to produce a woven bandage fabric and is then held in a relaxed condition to allow shrinkings to occur.

Suitable treatments include passing the fabric in a tensionless state through a steam box followed by a hot air dryer. Alternatively the fabric can be plaited loosely and allowed to relax naturally at room temperature for at least 12 hours. Such processes can advantageously allow the treatment of continuous lengths of bandage fabric.

Continuous lengths can then be cut into individual lengths.

The spooling tension of the yarn prior to relaxation is usually measured as a function of the diameter of the loaded spool relative to the stretched length of the fabric. Thus the diameter of the spooled bandage is from 40 to 70 mm for a length of bandage of from 4 to 4.5 m.

For example, a heavy-weight bandage of 4.5 m in length; preferably has a spooled diameter of from 50 to 70 mm, e.g. 60 mm. A light-weight bandage of 4 m in length preferably has a spooled diameter of from 40 to 60 mm, e.g. 50 mm.

During the process of relaxation the textured filament warp yarns relax or shrink whilst the staple fibre yarns which do not possess elasticity do not shrink. Thus they form loops thereby forming the "crepe effect" on both surfaces of the bandage.

Therefore, in a further aspect the present invention provides a woven bandage which exhibits a crepe effect in the form of loops of staple fibre yarn on the surface of the bandage.

The surface loops of staple fibre yarn, for example, cotton yarn advantageously provide the bandage of the invention with a "soft feel" and an absorbent surface. The textured yarns advantageously provides the bandage of the invention with good elastic stretch properties and the bulky nature of the yarn also provides the bandage with good cover properties.

The bandage of the invention does not employ high twist cotton yarns and therefore does not suffer from the harsh feel and high cost problems associated with such high twist yarns.

The present invention will now be illustrated, but in no way limited, by reference to the following drawings.

Figure 1:
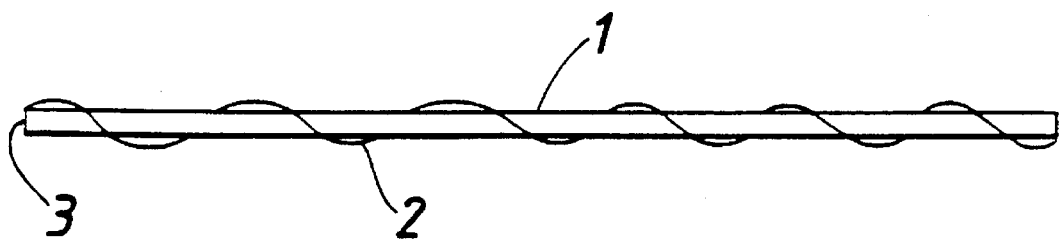
FIG. 1 is a schematic view of a composite warp yarn of the invention prior to relaxation.

FIG. 1 illustrates a composite warp yarn (1). Composite yarn (1) comprises staple fibre yarn (2) such as a cotton yarn and a textured filament yarn (3) such as textured polyamide yarn which are twisted together. The composite yarn (1) is shown in a tensioned state after being woven into a bandage.

Figure 2:
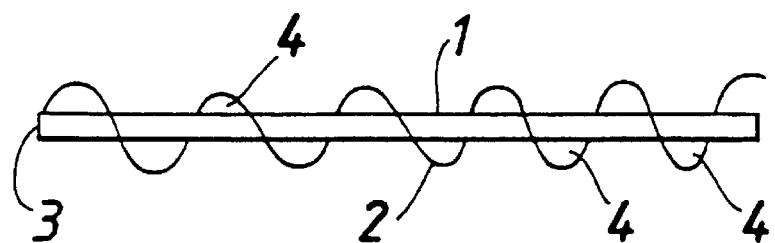
FIG. 2 is a schematic view of a composite warp yarn of FIG. 1 after relaxation.

FIG. 2 illustrates the composite yarn (1) of FIG. 1 after relaxation for example after treatment in a relaxed state in a heated oven. During treatment of yarn (1) the textured filament yarn (3) shrinks. The staple fibre yarn (2) has no elastic properties and therefore on relaxation the staple fibre yarn (2) forms loops (4).

Figure 3:
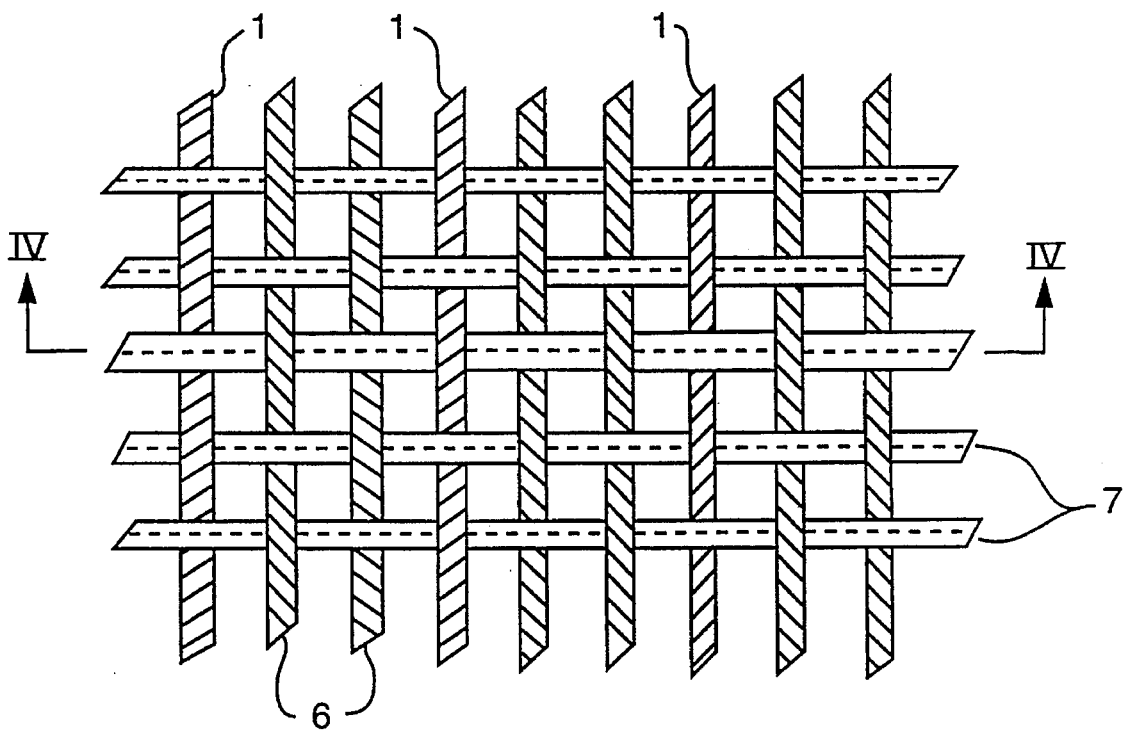
FIG. 3 is an enlarged plan view of a portion of the bandage fabric.

FIG. 3 illustrates a portion of the bandage fabric which is composed of composite warp filaments (1), textured warp filaments (6) and weft filaments (7). The particular bandage fabric illustrated in FIG. 3 has an equal number of picks and ends per 10 cm. For example, this bandage may contain 100 ends per 10 cm and 100 picks per 10 cm.

Figure 4:
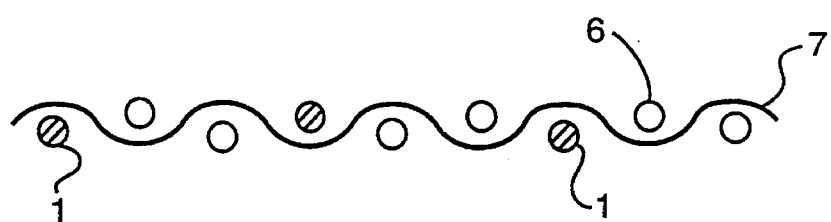
FIG. 4 is an enlarged side view of the bandage fabric in cross-section along the line IV—IV in FIG. 3.

FIG. 4 illustrates a side view of the bandage fabric in cross-section showing the composite warp filaments (1), textured warp filaments (6) and the cross-section of a weft filament (7).

In use, composite yarns (1) may be used as warp yarns in the weaving of crepe effect bandages. Upon relaxation from a stretched state, loops (4) provide the bandage of the invention with a soft feel and a crepe effect.

The present invention will now be illustrated by the following examples.

EXAMPLE 1

A light-weight woven bandage of the invention was formed from a woven fabric produced on a narrow fabric loom using a 1:1 ratio of cotton/nylon composite and nylon warp yarns (145 ends/10 cm) and cotton weft yarns (70 picks/10 cm). The cotton and nylon yarns used in this example were 19.68 Tex staple fibre cotton yarn and 2/78 D Tex textured nylon filament yarn respectively. The composite warp yarns contain the cotton and nylon yarns twisted together (125 turns/meter).

The woven fabric in a relaxed state was then subjected to a conventional steam bath to bulk the fabric before being wound into a roll. The bandage was 10 cm wide, exhibited crepe effect and had an elastic stretch in the warp direction of 70%. The bandage had a weight per unit area of 53.5 g/m².

The bandage was found to have a relatively soft feel and also had an aesthetically appealing appearance due to the crepe effect and the cove provided by the bulked fabric and yarns.

EXAMPLE 2

A heavy-weight bandage of the invention was made in the same manner as Example 1 except that the woven fabric contained 152 ends/10 cm of warp yarns which were composite cotton/nylon yarns and the weft yarns were 36.9 Tex cotton yarns.

The bandage of this example had a similar soft feel and appealing appearance as that of Example 1. The bandage had a weight per unit area of 82.5 g/m².

Bandages of Examples 1 and 2 were applied around the lower part of legs of volunteers. The bandages were found to be highly conformable, comfortable to wear and capable of exerting low compression to protruding areas, i.e. the calves of the legs.

I claim:

1. A woven bandage which exhibits a crepe effect characterised in that the bandage contains textured filament warp yarns and composite warp yarns comprising a staple fibre yarn and a textured filament yarn twisted together.

2. A woven bandage which exhibits a crepe effect and which comprises composite warp yarns aligned in a warp direction and weft yarns aligned in a weft direction woven together to form a bandage having a unit area wherein the composite warp yarns comprise a staple fibre yarn and a polyamide or polyester textured filament yarn loosely twisted together.

3. A woven bandage according to claim 2 in which the staple fibre yarn comprises a staple cellulosic fibre yarn.

4. A woven bandage according to claim 2 in which the staple fibre yarn comprise hydrophilic.

5. A woven bandage according to claim 2 in which the textured filament yarn comprises a synthetic fibre polymer.

6. A woven bandage according to claim 2 in which the textured filament yarns have a crimp rigidity of from 20–50%.

7. A woven bandage according to claim 2 in which the twist level for the composite yarn is 60 to 200 turns/meter.

8. A woven bandage according to claim 2 in which the twist level for the composite yarn is 125 turns/meter.

9. A woven bandage according to claim 2 wherein the bandage comprises weft yarn of a staple fibre yarn.

10. A woven bandage according to claim 2 having a weight per unit area of 40 to 120 g/m².

11. A woven bandage according to claim 2 containing 100 to 200 ends per 10 cm.

12. A woven bandage according to claim 2 containing 50 to 110 picks/10 cm.

13. A woven bandage according to claim 2 adapted to stretch in the warp direction by at least 50% of its original length.

14. A process for making a woven bandage according to claim 2 which comprises treating a woven bandage fabric containing composite warp yarns comprising a staple fibre yarn and a textured filament yarn to shrink the fabric in the warp direction.

15. A woven bandage according to claim 2 which, when spooled, has a diameter which is from 40 to 70 mm for a length of bandage of from 4 to 4.5 m.

16. A bandage which comprises 19.68 Tex cotton/2/78 D Tex polyamide composite warp yarns which alternate with 2/78 D Tex polyamide warp yarns and 19.68 Tex cotton weft yarns characterised in that the composite warp yarns comprise a staple fibre yarn and a textured filament yarn twisted together.

17. A bandage which comprises 19.68 Tex cotton/2/78 D Tex polyamide composite warp yarns only and 36.9 Tex cotton weft yarns characterised in that the composite warp yarns comprise a staple fibre yarn and a textured filament yarn twisted together.

18. A composite yarn characterised in that the composite yarn comprises a staple fibre yarn and a textured filament yarn twisted together, the twisted composite yarn having from 60 to 200 turns/meter.

19. A composite yarn characterised in that the composite yarn comprises a cotton yarn and a textured yarn twisted together, the twisted composite yarn having from 60 to 200 turns/meter.

20. An article of manufacture comprising a bandage material which exhibits a crepe effect and which contains composite warp yarns aligned in a warp direction and weft yarns aligned in a weft direction woven together, wherein the composite warp yarns comprise a staple fibre yarn and a polyamide or polyester textured filament yarn loosely twisted together.

21. A method of treatment of one or more of the following disorders; namely, varicous veins, lymphodoeama, muscle strain or muscle sprain, which comprises applying an article according to claim 20 to the affected site on a patient.

* * * * *